United States Patent [19]
Pokras

[11] Patent Number: 5,647,851
[45] Date of Patent: Jul. 15, 1997

[54] METHOD AND APPARATUS FOR VIBRATING AN INJECTION DEVICE

[76] Inventor: Norman M. Pokras, 4448 Village Rd., Long Beach, Calif. 90808

[21] Appl. No.: 489,353

[22] Filed: Jun. 12, 1995

[51] Int. Cl.⁶ .................................................. A61M 37/00
[52] U.S. Cl. .................................................. 604/131; 604/22
[58] Field of Search ........................ 604/131, 151, 604/154, 155, 253, 20, 22

[56] References Cited

U.S. PATENT DOCUMENTS

2,258,857  10/1941  McCann .
2,525,398  10/1950  Collins .
3,308,823  3/1967   Peterson .
3,620,209  11/1971  Kravitz .

Primary Examiner—Michael A. Brown
Assistant Examiner—Justine R. Yu
Attorney, Agent, or Firm—Fulwider Patton Lee & Utecht, LLP

[57] ABSTRACT

A vibrating injection device includes a housing formed with an interior chamber for releasably housing a conventional syringe therein and further including an opening on one end thereof. A syringe vibrating motor is also disposed in the interior chamber adjacent the syringe to vibrate same. A plunger drive motor is housed in the interior chamber and is connected to the plunger of the syringe to manipulate the plunger to expel the contents of the syringe through the needle.

26 Claims, 3 Drawing Sheets

METHOD AND APPARATUS FOR VIBRATING AN INJECTION DEVICE

BACKGROUND OF THE INVENTION

1. Field of the Invention

The present invention relates to devices for administering medicinal fluids to patients and, more particularly, to a device for releasably carrying and selectively vibrating a syringe needle during the administration of medication to a patient.

2. Description of the Prior Art

The administration of some type of medication to patients is useful, if not necessary, in many different situations, and especially during the course of many different medical and dental procedures. Medications can be administered in a variety of different ways, such as orally, by inhalation, or by injection through a needle. Injections are in many cases the preferred means of delivery due to the short time lapse between the injection of the medication and the resulting benefit to the patient. The benefit can be realized almost instantly because the medication can be injected directly to the desired area, or may be directly injected intravenously into the patient's bloodstream. This can be contrasted with medication taken orally where there is typically a substantial delay while the ingested medication is fully digested and delivered to the desired site within the patient's body.

Injections can be of many types, such as intravenous, intramuscular and infiltration. In addition to the overall preference for injections, the administration of medication to trauma patients by means of an injection is a necessity in situations where time is critical to saving the patient's life.

Although the injection of medication has many benefits and efficiencies, it is, in most cases, one of the least preferred method for the patient to receive medication. In the administration of most injections, there is some associated pain and discomfort caused by piercing of the skin by the needle and by forcing medication into the tissue. As a result of being subjected over the years to many such painful and uncomfortable injections, many patients harbor a fear of, and apprehension toward, such injections. Some patients refuse to receive injections, while others simply delay, or altogether avoid, seeking medical or dental attention rather than face the possibility of being subjected to an injection. In addition, many small children have a much lower threshold of pain than adults. Thus, what might be deemed merely an uncomfortable injection for an adult can be viewed as dehabilitatingly painful by a child, thus adding to the difficulty in effectively and efficiently administering an injection.

These factors are compounded in the practice of dentistry, and particularly oral surgery, where multiple applications may be required, many of which must be administered in locations that are difficult to access, such as for the mandibular site. Studies have proven that a great part of the patient's apprehension stems from the fear aroused when he or she observes the physician, after the needle has penetrated to the desired location, reaching for and depressing the plunger to eject the medication.

Thus, there has been a long-standing need for a device which may safely and effectively reduce the pain and discomfort associated with an injection of medication and thus substantially reduce the fear of and resistance to such injections. The conventional method, still widely practiced today, is to simply fill a conventional syringe with the medication to be delivered to the patient, apply a topical anesthetic, pierce the patient's skin with a needle carried at one end of the syringe to access tissue or a vein, and eject the medication through the needle into the tissue or vein. This procedure produces much of the fear and apprehension experienced by patients because there is no alleviation of the pain and discomfort associated with either the penetration of the needle or injection of the medication. For injections forced under pressure of the syringe plunger into the tissue, such as in the patient's gum area, much of the pain stems from ballooning of the medication in the tissue adjacent the needle tip. Thus, there exists a need for a syringe device that will accelerate the rate at which the ballooned medication is migrated into the tissue for absorption thereby easing the associated pain.

A device proposed in attempt to reduce the pain and discomfort associated with injections includes a vibrating contact element for placement against the skin of the patient adjacent the area to receive the injection. Vibration of the contact element against the patient's skin purportedly serves to distract and confuse the patient's nerve functions, thus relieving the pain normally experienced during an injection. This device is not free from shortcomings, however. The device is bulky and cumbersome, requiring two hands to maintain the contact element pressed against the patient's skin while actuating the vibration means to vibrate such contact element. Thus, either an assistant is required to handle the device while the doctor or dentist performs the injection, or the patient must handle the device himself or herself. In addition, the device provides no vibration to the needle itself. As such, it only serves to act upon the surface skin thereby limiting the effectiveness for injections penetrating deeper below the skin.

Another device envisioned to utilize vibration in a medical procedure is an apparatus for inoculation against smallpox and the like. A form of such device is shown in U.S. Pat. No. 3,308,823 to Peterson. This device includes a vaccine dispenser and a separate vibrating needle to serve as a skin scratching mechanism. Thus the vaccine is dispensed in a location on the surface of the patient's skin through the dispenser and the needle vibrated in such spot to create small ruptures thereon so the vaccine may be drawn under the patient's skin. This device, while serving as a surface scratching apparatus, provides no means for deadening the patient's nerves against pain or for injecting a vaccine or other medication deep into a patient's tissue or into a vein or artery and thus is limited in its usefulness.

Yet another device proposed in attempt to alleviate the pain and discomfort associated with injections includes a vibrating casing formed with a central opening and including a pair of connectable straps attached to opposite ends of the casing. The casing is intended to be placed against the patient's skin encircling the area to receive the injection and the straps wrapped about the patient body and connected to hold the casing firmly against the patient's skin. Vibration of the casing purportedly reduces the pain and discomfort typically associated with the injection. This device suffers the shortcoming that it provides no vibration to the needle itself, and thus only acts upon the surface of the skin. In addition, the device may not be efficiently used in connection with injections to be administered inside the mouth, thus severely limiting its use in most dental procedures.

As such, it may be appreciated that there continues to be a need for a vibrating syringe device which is convenient to use and effective to reduce the pain and discomfort associated with injections. There would be substantial benefit in such a device having the characteristic of concealing operation of the plunger from the patient's perception to thereby minimize the patient's apprehension. The instant invention addresses such needs.

SUMMARY OF THE INVENTION

Briefly, and in general terms, the present invention is in the form of a portable, hand held vibrating injection device comprising a housing formed with an interior chamber. Housed in the interior chamber is a vibrator comprising a motor and weighted shaft for vibrating a syringe and needle. The vibrator may be activated as the needle is advanced to penetrate the surface skin of the patient to reduce the amount of pain and discomfort which would otherwise be experienced. In one embodiment, a second motor is housed in the interior chamber to rotate a threaded drive rod connected to the syringe plunger to drive such plunger at a predetermined rate to expel the medication through the needle at a measured rate while the first motor vibrates such needle to vibrate the pool of ejected medication ballooning up in subcutaneous tissue adjacent the needle tip to accelerate migration of such medication into the tissue and away from the balloon at the needle tip.

Other features and advantages of the invention will become apparent from the following detailed description, taken in conjunction with the accompanying drawings which illustrate, by way of example, the features of the invention.

DETAILED DESCRIPTION OF THE PREFERRED EMBODIMENT

Figure 1:
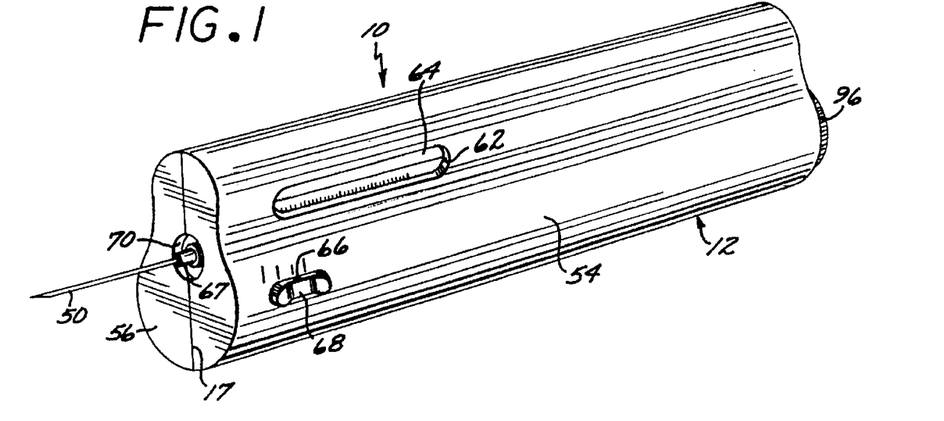
FIG. 1 is a perspective view of a vibrating injection device embodying the present invention.
Figure 6:
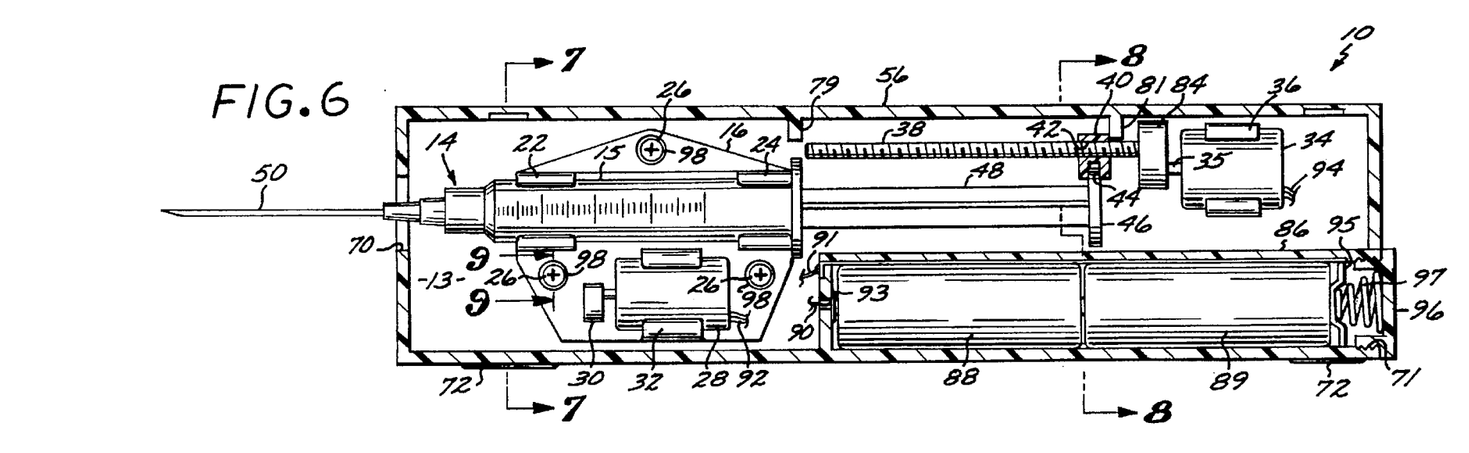
FIG. 6 is a longitudinal sectional view, in enlarged scale, of the vibrating injection device shown in FIG. 1.
Figures 7, 8:
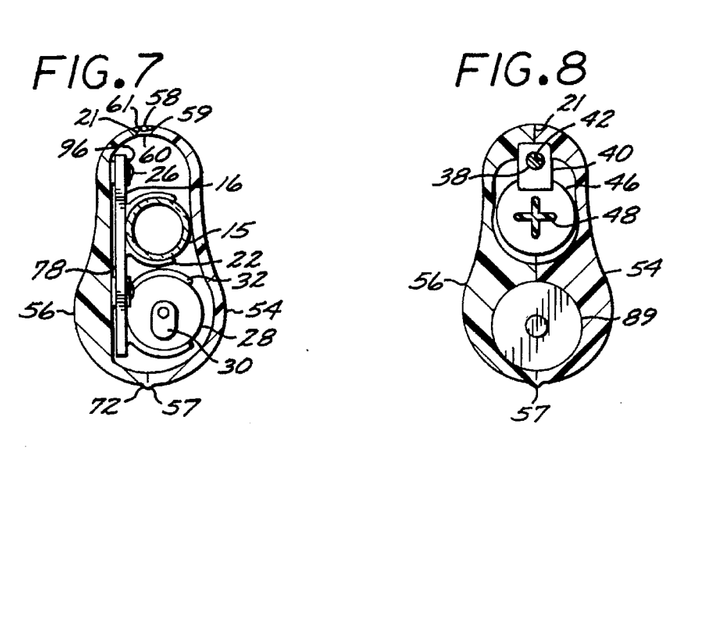
FIG. 7 is a transverse sectional view taken along the line 7—7 of FIG. 6.
FIG. 8 is a transverse sectional view taken along the line 8—8 of FIG. 6.

In the following detailed description, like reference numerals will be used to refer to like or corresponding elements in the different figures of the drawings. Referring now to the drawings, and particularly to FIGS. 1 and 6, there is shown generally a vibrating injection device 10 embodying the present invention. The vibrating injection device comprises, generally, a tubularly shaped housing 12 formed with an interior compartment 13 for removably housing therein a conventional disposable syringe 14 carried from a longitudinally projecting mounting board 16 (FIG. 7). The conventional syringe includes a storage barrel 15 which carries on one end a metallic injecting needle 50 and telescopically accepts in the opposite end a plunger 48 including a first end formed for a close fit within the barrel to serve as a piston therein and a second end defining an end flange 46. The syringe is preferably releasably mounted to such mounting board 16 by means of a pair of longitudinally spaced apart C-shaped clips 22 and 24 formed for complemental engagement with and gripping of the barrel 15 of the syringe. The mounting board in turn is fixedly attached to an inside wall 78 of the housing by means of a plurality of machine screws 26 which engage respective threaded bores 80 formed on such wall. Mounted forwardly on the mounting board 16 is a syringe vibrating DC motor 28 (FIG. 6) including an eccentrically weighted drive shaft 30 which serves to supply vibration to the mounting board and thus to the syringe during operation of the motor. Conveniently, the motor is driven by a pair of double A dry cell batteries 88 and 89 mounted rearwardly in the housing.

It has been common practice in the medical field, both in injecting anesthetic to a patient's gums or in penetrating the skin or a vein, to utilize a conventional syringe incorporating a metallic needle typically formed at its distal end with a bevel cut to leave a sharp point on one diametrical side. In the case of injecting an anesthetic in, for instance, a patient's gum, the dentist will typically apply a topical anesthetic to the surface of the gum and then, possibly while endeavoring to conceal the syringe from view by the patient, approach the gum site with the point of the needle. The needle is typically then forced through the gum surface tissue. Different medical technicians employ different procedures for this application, all designed to minimize trauma and pain to the patient. All such techniques involve popping the needle point through the gum skin, an area that typically has highly sensitive nerves. Consequently, the patient often is exposed to considerable pain during this entry procedure. After subcutaneous entry, the needle point is maneuvered to the desired location for application of the anesthetic. The plunger is then typically depressed under the force of the dentist's palm to force the medication through the lumen of the needle to be forced into the gum tissue for the purpose of anesthetizing the site. It has been shown that a great deal of pain may be experienced after subcutaneous entry and during forced injection of the anesthetic into the gum tissue. It is understood that the anesthetic forced from the tip of the needle tends to pool near the tip of the needle creating somewhat of a balloon effect within the tissue. The volume of anesthetic so ballooned at this site is then slowly absorbed into the surrounding tissue to slowly reduce such balloon effect.

I have discovered that by actuating the syringe vibrating motor 28 as the point of the needle 50 makes contact with the epidermis of the body skin or gingiva of the gum, the vibration imposed on the tip of the needle serves to, not only distract the patient's attention from the anticipated pain associated with penetration of the surface, but facilitates the needle entry through the epidermis and gingiva as the case may be. The action of the sharp needle point in making tiny rotary strokes provides an efficient effective cutting effect comparable to the reciprocating stroke of a knife. The needle point thus progressively cuts its way through the epidermis and subcutaneous tissue without the necessity of applying the axial force normally associated with a puncture entry. Additionally, the vibratory action of the needle will tend to vibrate the skin and nerves thus tending to dull the nerve sensitivity in the local area so that the pain sensation is minimized, if not totally eliminated. I have further discovered that by continuing to vibrate such needle 50 after subcutaneous entry and during injection of the anesthetic into the gum, the migration of the anesthetic away from the tip of the needle is accelerated thus minimizing the aforedescribed ballooning effect and the consequent pain associated with such ballooning effect.

Figure 12:
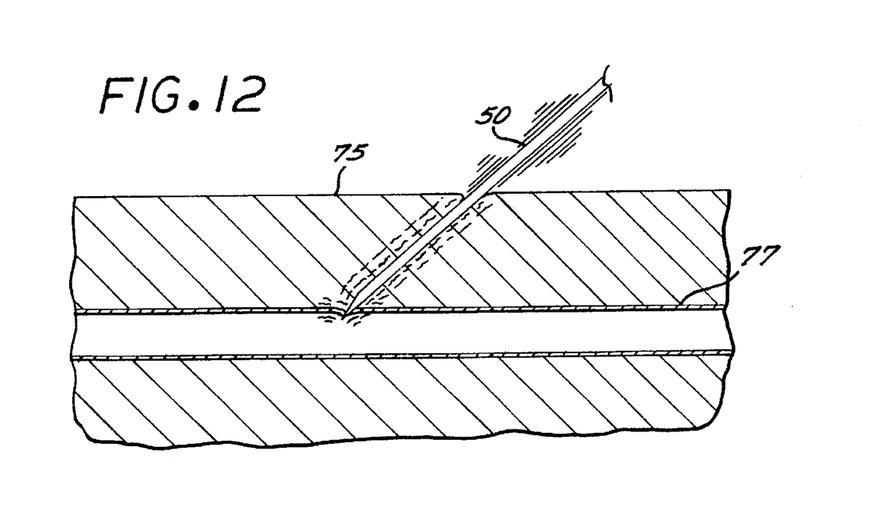
FIG. 12 is a vertical sectional view of a vibrating injecting needle carried by the vibrating injection device of FIG. 1 penetrating into the vein of a patient.

Referring to FIG. 12, in making penetration for intravenous applications, such vibration of the needle 50 enhances the gradual penetration of the needle tip through the patient's skin 75 and through the wall of the underlying blood vessel 77. I have selected a vibration rate of 60 cycles per minute which I have found particularly useful in reducing the sensitivity of the nerves and in facilitating penetration by the needle tip. The action of such vibration is so effective in enhancing penetration as to overcome many of the difficulties associated with penetrating what is normally termed a "rolling vein". It seems that with this rapid vibration of the needle tip the mass of the vein itself offers sufficient inertia to resist oscillating at such a high frequency with the tip of the vibrating needle so as to cause such tip to oscillate rapidly relative to the vessel wall to, in progressively nearly microscopic progression, work the sharp tip back and forth on a vessel to saw its way therethrough, while applying only minimal lateral force. This then serves to provide for the wall of the vessel to be penetrated under the influence of the vibrating needle tip, with only a minimal axial force being applied to the vessel wall to thereby minimize the action of the force applied to the vessel along the extended axis of the needle. Thus, the axial needle force necessary to puncture the wall of the vessel is minimized thereby minimizing the tendency of such force to shift the vessel from one side or the other of the extended axis of the needle.

In one embodiment of the present invention, the interior compartment 13 further houses a plunger drive motor 34 disposed rearwardly of the mounting board and mounted to the inside wall 78 of the housing by means of a C-shaped clip 36 (FIG. 6). The motor includes a shaft 35 coupled through a gear housing 84 to the back of a threaded drive rod 38 projecting parallel forwardly over the syringe plunger 48. A plunger coupling clip 40 is formed with a threaded through bore 42 to be received on such drive rod to be displaced therealong during rotation of such drive rod. The plunger coupling clip is further formed with a crevice defining a downwardly opening slot 44 to engage over the top edge of the plunger flange 46. Thus with the plunger coupling clip engaged with the flange of the plunger, activation of the plunger drive motor 34 serves to rotate the drive rod to thereby displace the plunger coupling clip along such rod, thereby driving the plunger into the barrel to expel the contents stored therein through the needle.

The housing 12 may be constructed of hard plastic and is somewhat figure-eight shaped in cross section to define a lower tubular section for housing rearwardly therein the portable power batteries 88 and 89 and to form an upper tubular section for receipt of the plunger drive motor 34. The housing is partially hollowed out to define the interior compartment 13 (FIGS. 6, 7 and 8).

The housing 12 is split longitudinally to form a pair of clam shell halves 54 and 56 connected together on their bottom sides by a longitudinally extending living hinge 57 (FIG. 7). In the preferred embodiment, one-sided adhesive strips of polyethylene 72 are adhered to the bottom wall of the housing to act as hinge reinforcing plates (FIGS. 6 and 7). Thus, the strips will provide a flexible member operative to reinforce the living hinge 57 or, in the event the material defining such hinge breaks, serve as the primary hinge element.

The top edges of the respective housing halves 54 and 56 are configured to be disposed in confronting relationship and the half 54 is constructed with a pair of longitudinally spaced part thin, laterally projecting longitudinal resilient clips 60 configured with respective upwardly opening longitudinally extending grooves 61 and terminating at their respective distal edges with downwardly and laterally sloped latch ramps 21 (FIG. 7). The confronting edge of the housing half 56 is configured with respective complementally shaped downwardly opening pockets configured with respective top walls 58 configured with respective longitudinally extending downwardly projecting cleats 59 releasably received in the respective upwardly opening groove 61.

Referring to FIG. 1, the half 54 has formed forwardly in the longitudinal side wall thereof a longitudinal slot 62 defining a window into which is placed a lens 64 and through which the barrel 15 of the syringe 14 may be viewed. Thus during the use of the vibrating injection device 10 the operator may readily determine the amount of medication stored in the syringe and thereby determine the amount of medication which has been delivered to the patient without the need for interrupting the procedure to inspect such barrel.

The half 54 is further formed low in the forward portion of the side wall thereof with a generally oval slot 66 for projection therethrough of a control switch thumb rocker 68 as described in more detail below (FIG. 1).

Figure 2:
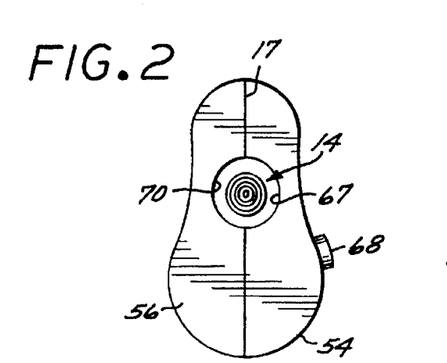
FIG. 2 is a left end view, in enlarged scale, of the vibrating injection device shown in FIG. 1.
Figure 3:
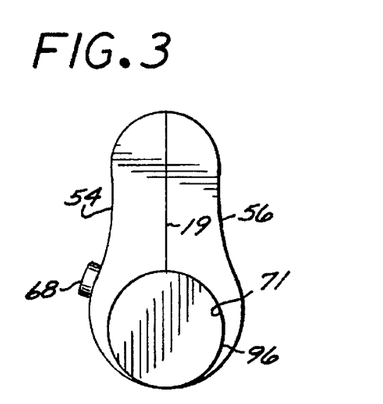
FIG. 3 is a right end view, in enlarged scale, of the vibrating injection device shown in FIG. 1.

The housing halves 54 and 56 have formed generally centrally in the respective front walls thereof respective generally semi-circular confronting needle way openings 67 and 70 aligned concentrically with the C-shaped clips 22 and 24 when the housing is closed for projection therethrough of the injecting needle 50 (FIGS. 1 and 2).

Figure 4:
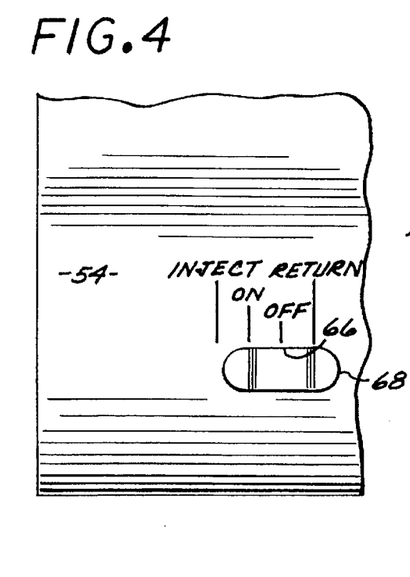
FIG. 4 is an enlarged, detailed side view of the vibrating injection device shown in FIG. 1.

It will be appreciated by those skilled in the art that the switch control rocker 68 may take many different forms such as a rocker, slider, push bar or rotary. For purposes of illustration, I have shown a multiple position rocker switch but for some applications it will be appreciated that a slider switch will be preferable. Referring to FIG. 4, there is illustrated the rocker 68 of the control switch which projects through the slot 66 formed on the side wall of the half 54. The switch may be manually shifted from the "OFF" to either the "ON", "INJECT" or "RETURN" positions to select activation of the syringe vibrating motor 28 and the plunger drive motor 34 as described in more detail below.

Figure 5:
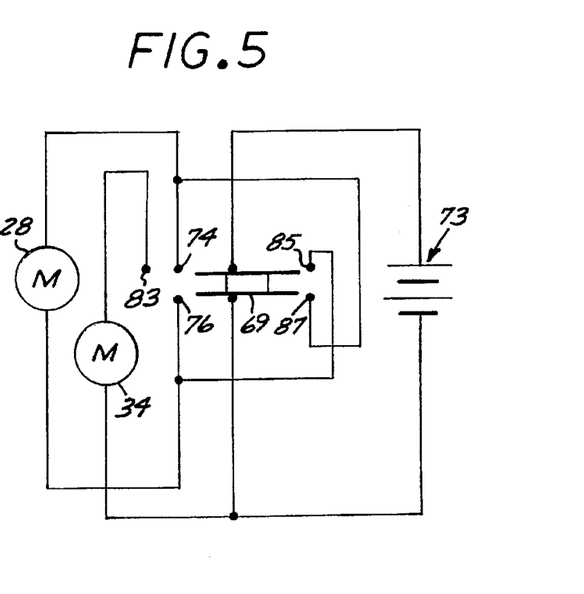
FIG. 5 is a schematic diagram of the electrical circuitry included in the vibrating injection device shown in FIG. 1.

Referring to FIGS. 5 and 6, the batteries 88 and 89 are connected in series with one another and are connected across the respective motors 28 and 34 by means of an electric circuit including the power source 73 defined by such batteries and a control switch including the rocker arm 68 and contact 69 which are shown diagrammatically as shiftable to the "ON" position engaging the contact 69 with the terminals 74 and 76 to connect the motor 28 across the terminals of the power source 73. The rocker 68 is further shiftable to the left in FIG. 4 to the "INJECT" position where it places the contact 69 in contact with terminals 74, 76 and 83 of the circuit to connect both motors 28 and 34 across the terminals of the power source 73 thereby actuating both motors to simultaneously vibrate the needle 50 and drive the drive rod 38 in a forward direction to advance the coupling clip 40 to the left as shown in FIG. 6 to thereby depress the plunger 48.

With further reference to FIGS. 4, 5 and 6, the rocker 68 is shown for illustrative purposes as shiftable to the right of the "OFF" position to the "RETURN" position where such rocker places the contact 69 in contact with terminals 85 and 87 of the circuit to connect the respective leads of the motor 28 to the opposite terminals of the power source 73 as when the rocker is in the "ON" position. As such, the motor will actuate to rotate the threaded drive rod 38 in a direction opposite of that when the rocker is in the "ON" position, thereby driving the coupling clip 40 to the right along the drive rod as shown in FIG. 6 until it contacts and stops against the flange 81, thus returning such clip to its home position.

Figure 9:
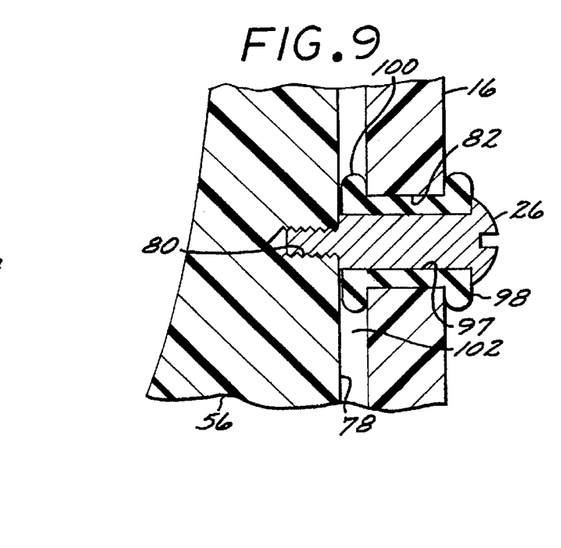
FIG. 9 is an enlarged, detail view taken along the line 9—9 of FIG. 6.

Referring to FIGS. 6, 7 and 9, formed on the inside wall of the housing half 56 are three threaded bores 80 arranged in a triangular pattern. Received in the respective bores are the tips of machine screws 26 to fixedly attach the mounting board 16 to the half 56.

In the preferred embodiment, the mounting board 16 is a substantially planar and constructed piece of a rigid material such as metal or plastic. A plurality of spaced apart machine screw bores 82 are formed thereon in a predetermined triangular pattern to correspond with the triangular configuration of the bores 80 formed on the inside wall 78 of the half 56. Respective barrel shaped sleeves 98 are received in the respective bores 82 and are formed at their opposite ends with radially outwardly flared flanges 100 (FIG. 9). The bores 97 of such sleeves are formed for slip fit receipt of the shanks of the respective screws 26.

Referring to FIGS. 6 and 8, in order to ensure that the plunger coupling clip 40 is maintained in its upright position within the housing 12, a longitudinally projecting downwardly opening groove 41 defines a guide track at the top interior of the compartment 13 projecting parallel with the drive rod 38 for slidable receipt therein and displacement therealong of such clip.

With continued reference to FIG. 6, the opposite ends of such track 41 are defined by a pair of spaced apart, downwardly projecting flanges 79 and 81. Such flanges define respective coupling clip stops which serve to limit the travel of the plunger coupling clip 40. As such, travel of the plunger 48 will be restricted to prevent it from being drawn so far rearwardly as to be withdrawn from the syringe barrel.

With further reference to FIG. 6, the housing 12 is formed rearwardly in the lower portion of the compartment 13 with a generally cylindrical, hollow casing 86 for telescopical receipt in stacked relation of the dry cell batteries 88 and 89 defining the power source 73. Included at the front and rear of such casing are respective conventional battery contacts 93 and 95 connected with respective electric leads 90 and 91 leading to the rocker 68 of the control switch.

The casing 86 is open at its back end where it is internally threaded at 71 for receipt of the externally threaded stub barrel of a cap 96 mounting the back end of a coiled battery compression contact spring 97 which carries the electrically conductive disk contact 95 at its forward end to bias the batteries forwardly into contact with one another (FIGS. 2 and 6).

Referring to FIG. 6, the syringe vibrating motor 28 is shown mounted from the mounting board 16 by the C-clip 32 with the eccentrically weighted shaft 30 projecting forwardly therefrom. As such, operation of the motor will apply a primarily lateral vibration to the mounting board and syringe 14 to thus orbit the needle tip primarily in a plane perpendicular to the needle axis. It will be appreciated that the orientation of the clip 32 mounting such motor could be rotated 90 degrees with respect to the housing 12 such that the weighted shaft would project laterally within the housing to thereby apply a primarily longitudinal vibration to the syringe consequently applying a primarily longitudinal reciprocation to the needle 50.

It will further be appreciated that the clip 32 mounting such syringe vibrating motor 28 could be rotated to orient the weighted shaft 30 at an angle somewhere between the position shown at 90 degrees thereto, as for example 45 degrees to the longitudinal axis, to thereby apply combined lateral and longitudinal vibrations to the needle 50. In addition, in place of the single syringe vibrating motor, a pair of such motors may be mounted to the mounting board 16, the respective motors having different orientations so that one such motor creates a lateral vibration and the other creates a longitudinal vibration of the syringe.

In use, the vibrating injection device 10 of the present invention may be conveniently stored during periods of non-use and may be quickly and easily retrieved for use thereof. The operator may grasp the housing 12 and unlock the opposing tabs 58 and 60 to pull apart the respective halves 54 and 56 at their respective top sides to rotate about the living hinge 57 to gain access to the interior compartment 13 of the housing.

The operator may then select a conventional syringe 14 filled with the desired medication to be administered to the patient. In the event of use in a dental procedure, the medication selected will typically be an anesthetic. With the barrel 15 filled with such anesthetic, the plunger 48 will be in its fully extended rearward position as shown in FIG. 6. The operator may then insert the flange 46 of the plunger into the slot 44 formed on the plunger coupling clip 40 and insert the barrel 15 into the respective C-shaped clips 22 and 24 (FIG. 6). As such the needle will project from the front end of the housing 12 through the needle way openings 67 and 70. The operator may then draw the respective top sides of the housing halves 54 and 56 together and force such top sides together to engage the flange ramp 21 with the confronting edge of the clip 59 such that forcing such halves further toward one another will cause such clip to be driven into registration over the groove 61 to be snapped into place locking the housing closed (FIG. 7).

Figures 10, 11:
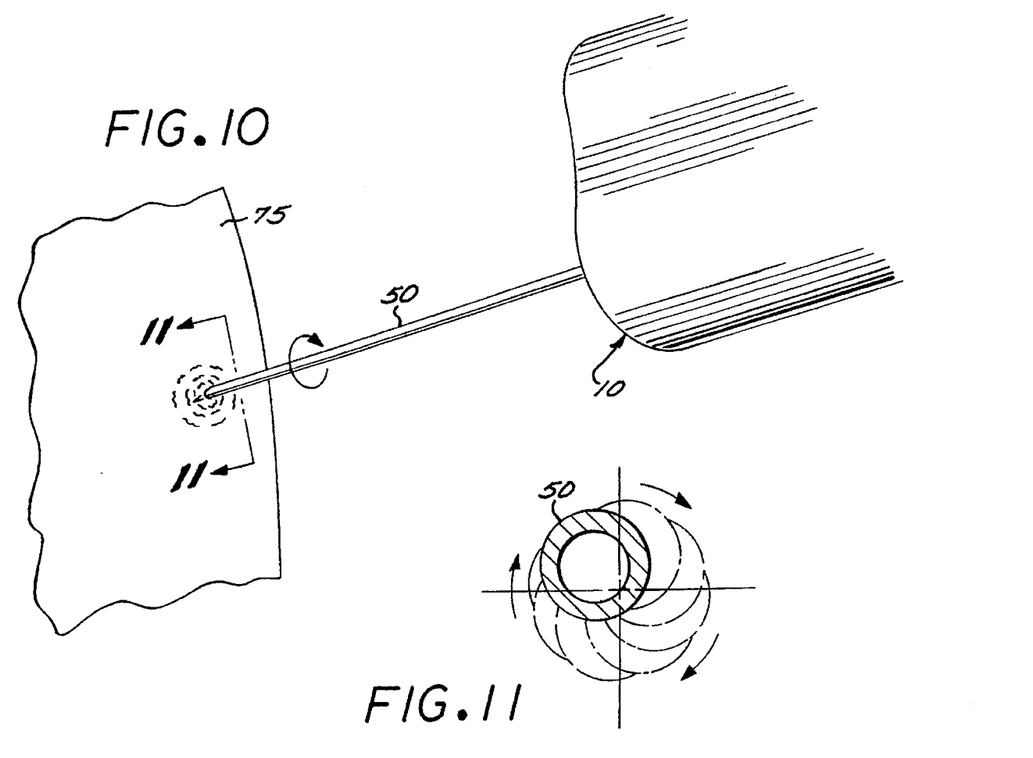
FIG. 10 is a fragmented perspective view of the vibrating injection device of FIG. 1 actuated and in position for piercing the gum surface tissue of a patient.
FIG. 11 is a transverse sectional view taken along the line 11—11 of FIG. 10.

The operator may then flip the rocker 68 of the control switch to the "ON" position, resulting in the activation of the syringe vibrating motor 28. The motor 28 will drive the eccentric drive shaft 30 causing the motor itself to vibrate in a path that might be considered primarily laterally about its longitudinal axis at a frequency of about 60 rpm. The vibration applied to the body of such motor 28 will act through the mounting screws 26 (FIGS. 6 and 9) by tending to shake or vibrate the mounting plate 16 in a manner dictated by the cushioning effect of the respective bushings 98. In the embodiment shown, the vibration is then transmitted to the barrel of the syringe 14 thus causing the needle 50 and, consequently, the tip thereof to orbit in a tiny orbit on the order of 3 micrometers in diameter (FIGS. 10 and 11) as influenced by the fact that the overall mechanism is not centered about a center of gravity thus resulting in some longitudinal vibration which, in practice, serves to enhance the overall performance of the needle in making initial penetration of the gum surface tissue and in assisting to numb the patient's nerves in the general proximity of the penetration site to thereby enhance the effectiveness of initial penetration and minimize the magnitude of the pain perceived by such patient. Additionally, as penetration continues while the dentist maneuvers the point of the needle 50 into the desired site adjacent the tooth where the dental work is to be undertaken, such vibratory action will serve to continue to enhance the effectiveness of the needle point in continuing to cut through the tissue to thereby minimize tearing of the tissue itself and minimize damage to the surrounding tissue site. It will be appreciated that the sharp leading edge of the needle 50, in being vibrated about a tiny orbital path, will serve to effectively slice the tissue in tiny strokes, all while vibrating the surrounding tissue to the full depth of penetration thus maintaining a numbing effect on the surrounding nerves to minimize the discomfort experienced by the patient.

It will be appreciated that this procedure is particularly important for administration of anesthetic to sites which are difficult to access and which might require the dentist to manipulate the syringe about in somewhat of an awkward position during the time the site is being accessed. An example would be in making a mandibular shot which for many dentists is recognized as somewhat of a challenging maneuver. That is, the patient's mouth might be packed with spacing and absorptive packing and the syringe needle maneuvered about between the cheek and gum to a location in the mandibular area where the gum tissue must then be penetrated at an acute angle with the surface of the gum while endeavoring to direct the needle tip deeper into the gum tissue toward the tooth area. It can be appreciated that, absent the benefits of the present invention, this maneuver may result in the needle tip taking a number of slightly different courses as the gum is penetrated thus adding to the pain experienced by the patient. For these applications, the benefits of the present invention are of particular utility.

Once penetration has been achieved to the desired depth in the patient's gum, the rocker 68 of the control switch may then be flipped to the "INJECT" position, so that while operation of the syringe vibrating motor 28 is continued, the plunger drive motor 34 will be energized. Such activation results in the rotation of the threaded drive rod 38 and thus the displacement of the plunger coupling clip 40 forwardly along such rod (FIG. 6). With the plunger coupling clip engaged to the flange 46, such flange is driven forwardly within the housing 12 to drive the plunger piston forwardly in the syringe barrel 15. The plunger piston thus drives the medication under high pressure slowly through the needle 50 to be ejected therefrom while such needle continues to vibrate. It has been discovered that this high frequency vibration of the needle 50 as the anesthetic is driven from the tip thereof serves to continue vibrating the surrounding tissue, as well as the mass of anesthetic being ejected. Such vibration serves to enhance the rate at which the fluid migrates anesthetic into such tissue thus accelerating disbursement of the anesthetic to the site of interest and minimizing the pain inflicted by the injection process. This procedure has been found to be particularly effective to reduce the tendency of the volume of fluid ejected from the tip of the needle to merely balloon up about such tip thus requiring the application of relatively high injection forces to apply sufficient pressure to the ballooned fluid to cause it to be forced into the fiber of the encapsulating tissue.

For the particular configuration shown, the pitch of the threads on the drive rod 38, the speed of the motor 34, and lumen of the needle 50 is selected such that the anesthetic is ejected from the tip of the needle at a rate of about 1.5 cubic centimeters per minute so that the rate of injection corresponds favorably with the capacity of the gum tissue of a normal patient to absorb the medication with the needle vibrated at a frequency of 60 cycles per minute. In this manner, the rate of injection is mechanically dictated to maintain a uniform rate which has been found favorable for a reasonably rapid injection while providing sufficient time for the ejected anesthetic to be absorbed in the tissue at the accelerated rate induced by the vibratory action of the needle.

A further benefit of the automatic needle actuator mechanism is the fact that the actuation of the syringe is achieved by the rather subtle act of the dentist's thumb on the rocker switch 68 in a relatively inconspicuous manner which will typically remain undetected by the patient. This then eliminates the apprehension typically attendant a patient's observation of the dentist's hand in making the maneuver to depress the syringe plunger. From a natural fear of the unknown, or from past experiences wherein pain has been associated with depression of the syringe plunger, patients tend to experience considerable apprehension when they perceive the syringe plunger is to be depressed. With my present invention, actuation of the plunger remains generally concealed from the patient's view thus removing the apprehension normally attendant plunger actuation.

It will be appreciated that the dentist may view the scale on the barrel of the syringe through the window 62 (FIG. 1) to measure the quantity of anesthetic injected. He or she may then manipulate the thumb rocker 58 to select the quantity of anesthetic injected during each actuation of the plunger actuator motor 34.

When injection of medication has been completed, the dentist may withdraw the needle from the patient's gum and shift the rocker 68 to the "RETURN" position to return the coupling clip to its home position. The rocker may then be shifted to the "OFF" position and the housing 12 opened as described above to remove the syringe 15 for disposal. The vibrating injection device may be closed and stored until it is to be used again.

As will be appreciated by those skilled in the art, for intravascular injection of local anesthetic, should there be any concern over location of the tip or the injection, the rocker may be switched to "return" to retract the plunger.

Referring to FIG. 12, it will be appreciated that the vibrating injection device of the present invention will likewise have utility in injecting other medications, such as those to be applied intravenously. In those instances, the needle of an I.V. line may be inserted in a holder comparable to that described above to be gripped by a holding clip or clamp similar to the clips 22 and 24 for temporary clamping thereof. The needle in that instance would be projected from the housing to be exposed such that vibration by the vibrating motor 28 will apply either a tiny orbital path to the sharp tip of the needle (FIG. 11) or an axially reciprocating path or some combination of the two. Then, as the physician or health technician approaches the I.V. site, as for instance in the forearm or in the groin area, the tip of the needle 50 will contact the epidermis to initiate penetration over the vein or artery to be accessed. Vibration of the needle will cause the tip of the needle 50 to travel about in a tiny orbital reciprocating path, or in the case of axial reciprocation, in an axial path, causing the needle tip to make tiny cutting strokes in the epidermis as the needle advances through the epidermis to the subcutaneous layers to thus rapidly vibrate the skin at about 60 cycles per minute as the tiny cutting path is made through the patient's skin 75 over the vein 77 being accessed. As the tip of the needle approaches the wall of the vein 77, the oscillating path of such tip will continue the incremental cutting strokes to rapidly cut through the wall of the vein. It will be appreciated that by cutting in this fashion, only a minimal axial force is applied to the wall of such vein by the needle. The tiny cutting strokes are effective to cut through the relatively tough wall of the vein without the normal high axial forces which have heretofore been associated with a puncture wound in a vein wall. It is important that the axial force necessary to advance the needle through the skin and through the wall of the vein is kept to a minimum thus minimizing the tendency of such axial force to cause the vein to tend to squirt to one side or the other of the needle tip as it is advanced through the patient's skin and against the vein. This characteristic is particularly important in the case of a patient having a "rolling vein" which may tend to otherwise roll away from the needle point thus typically necessitating multiple punctures of the skin and vein which in many instances causes great pain and discomfort to the patient and, from time to time, prevents access being had to the particular vein. Once the wall of the vein is accessed in this manner, the intravenous needle may be removed from the clamp or the holder comparable to the clips 22 and 24 and the vibrating housing will then be available for applications in other intravenous procedures.

It will be appreciated that the vibrating injection device of the present invention is compact and convenient to use. The device may take many different forms and may, for instance, incorporate a vibrator in conjunction with a refillable syringe, may incorporate an oscillating or reciprocating vibrator and may be used in conjunction with the automatic plunger actuator. The device may be of a portable nature as shown or may be driven by external AC or DC power.

While several forms of the invention have been illustrated and described, it will also be apparent that various modifications can be made without departing from the spirit and scope of the invention. Accordingly, it is not intended that the invention be limited, except as by the appended claims.

What is claimed is:

1. Vibrating injection apparatus for holding and vibrating an injection needle formed with a sharp tip and comprising:

an elongated housing formed with an interior compartment;

a syringe in said housing including a chamber for receipt of fluid medication and an injection needle having a sharp tip;

a mount assembly mounting said syringe in said housing;

a vibrator mounted in said housing and including a motor for vibrating said needle whereby said needle is mounted from said housing and said motor actuated to vibrate said needle as said needle is manipulated into position to penetrate the skin of a patient.

2. The vibrating injection apparatus of claim 1 wherein:
   said vibrator includes an eccentrically weighted shaft connected to said motor.

3. The vibrating injection apparatus of claim 2 further including:
   a power source electrically connected to said motor for supplying electric power to said motor.

4. The vibrating injection apparatus of claim 1 wherein said syringe includes a plunger and said vibrating injection device further includes:
   a plunger drive device in said compartment and including a threaded drive rod and an actuator motor for driving said drive rod;
   said plunger drive device further including a coupling comprising a plunger coupling clip formed with a threaded through bore for receiving said drive rod and further formed with a slot for releasably coupling with said plunger and further including:
   a DC battery in said housing; and
   a control switch on said housing electrically coupled to said battery, vibrator and actuator motor for selectively delivering power from said battery to said vibrator and actuator motor.

5. The vibrating injection apparatus of claim 4 wherein:
   said housing is formed with a cylindrical, hollow tubular compartment for storing said battery.

6. The vibrating injection apparatus of claim 1 further including:
   a window formed in said housing for viewing said syringe mounted from said mount assembly.

7. The vibrating injection apparatus of claim 1 wherein:
   said housing includes an inside wall formed with a plurality of spaced apart threaded bores and further including:
   a mounting board disposed in said interior compartment and formed with a plurality of spaced apart screw bores aligned with the respective said threaded bores;
   a plurality of screws received in the respective said screw bores to engage the respective said threaded bores to mount said mounting board to said inside wall; and
   a plurality of clips on said board for releasably mounting said syringe on said board.

8. The vibrating injection apparatus of claim 7 wherein:
   said screws are undersized to define respective shanks cooperating with the respective said screw bores to define respective annular spaces therebetween and wherein said apparatus further includes:
   a plurality of cushioning bushings received in the respective said annular spaces to cushion movement between said screws and board.

9. The vibrating injection apparatus of claim 1 wherein:
   said vibrator includes an electric motor including a shaft projecting parallel to said needle when said syringe is mounted from said mount assembly and an eccentric weight on said shaft.

10. The vibrating injection apparatus of claim 1 wherein:
    said vibrator is operative to vibrate said needle at a predetermined rate to, when applied to human nerves, effect at least some degree of numbness.

11. The vibrating injection apparatus of claim 1 wherein:
    said vibrator is operative to vibrate said needle at a cycle of substantially 60 cycles per second.

12. The vibrating injection apparatus of claim 11 wherein:
    said vibrator is operative to vibrate said needle through a path that includes a component transverse to the axis of said needle.

13. Hand held vibrating and injecting apparatus for housing a syringe including an injection needle and plunger comprising:

a hand held housing formed with an interior compartment and having an opening in one end;

a syringe including a barrel having a compartment for storing fluid therein and a needle having a sharp penetration point;

a mounting device in said compartment for releasably mounting said syringe for projection of said injection needle through said opening;

an electrically powered vibrator mounted from said housing for vibrating said syringe and needle;

a drive assembly housed in said housing and configured for engagement with said plunger and operative to drive said plunger relative to said syringe to expel said fluid from said barrel through said needle; and a power source housed in said interior compartment and electrically connected to said vibrator and to said drive assembly for supplying electric power to said vibrator and to said drive assembly.

14. The vibrating injection apparatus of claim 13 wherein:

said vibrator comprises a motor connected to an eccentrically weighted shaft.

15. The vibrating injection apparatus of claim 14 wherein said drive assembly comprises:

a plunger drive device mounted in said compartment and including a plunger drive motor and a threaded drive rod driven by said motor;

a plunger coupling clip formed with a threaded through bore for engagement with and displacement along said threaded drive rod during rotation of said threaded drive rod, said clip being further formed with a slot on one end thereof for releasable engagement with said plunger to thereby drive said plunger relative to said syringe during rotation of said threaded drive rod and further including:

a control switch electrically connected to said power source, vibrator and plunger drive motor for selectively delivering power from said power source to said vibrator and plunger drive motor.

16. The vibrating injection apparatus of claim 13 wherein:

said power source comprises at least one battery.

17. The vibrating injection apparatus of claim 16 further including:

a cylindrical, hollow casing formed in said housing for storing said battery.

18. The vibrating injection apparatus of claim 13 further including:

a window formed on said housing for viewing said syringe mounted in said interior compartment.

19. The vibrating injection device of claim 13 wherein:

said housing includes an inside wall formed with a plurality of spaced apart threaded bores and further including:

a mounting board disposed in said interior compartment and formed with a plurality of spaced apart screw bores aligned with the respective said threaded bores;

a plurality of screws received in the respective screw bores to engage the respective said threaded bores to mount said mounting board to said inside wall; and a plurality of clips mounted on said board for releasably mounting said syringe on said board.

20. The vibrating injection apparatus of claim 19 wherein:

said screws are undersized to define respective shanks cooperating with the respective said screw bores to define respective annular spaces wherein said device further includes:

a plurality of cushioning bushings received in the respective said annular spaces to cushion movement between said screws and board.

21. A method for penetrating a patient's tissue and for diminishing the pain while penetrating said tissue with a syringe device and injection needle formed with a sharp tip, said method including the steps of:

selecting a vibrator device including a vibrator for vibrating said needle at a predetermined frequency effective to, when applied to a patient's said tissue, impart a degree of numbness to said patient's nerves;

mounting said syringe to said vibrator device to, when said vibrator is actuated, vibrate said sharp tip at said predetermined frequency; and actuating said vibrator device while advancing said needle into said tissue to vibrate said tissue with said needle.

22. A method for penetrating a patient's tissue with a syringe and injection needle formed with a sharp tip, said method including the steps of:

selecting a vibrator device including a mount for receiving said needle and a vibrator for vibrating said needle in a path to cause said sharp tip, as it penetrates said tissue, to make short cutting strokes in said tissue in a direction transverse to the axis of said needle;

mounting said syringe in said vibrating device; and actuating said vibrator and advancing said device toward said tissue to cause said sharp tip to penetrate said tissue as said sharp tip is moved through said short cutting strokes.

23. A vibrating injection device holding and vibrating a syringe including a plunger and an injection needle having a sharp tip, said device comprising:

an elongated housing formed with an interior compartment;

a mount assembly for mounting said syringe in said housing with said needle projecting from said housing;

a vibrator mounted in said housing and including a motor for vibrating said syringe and needle;

a plunger drive device including a threaded drive rod and an actuator motor for driving said drive rod;

a coupling comprising a plunger coupling clip formed with a threaded through bore for threadedly engaging said drive rod and further formed with a slot for releasably engaging said plunger;

at least one battery in said housing; and a control switch on said housing electrically coupled to said battery, vibrator and actuator motor for selectively delivering power from said power source to said motor of said vibrator device and actuator motor.

24. The vibrating injection device of claim 23 wherein:

said housing is formed with a cylindrical, hollow tubular compartment for storing said battery.

25. The vibrating injection device of claim 23 wherein:

said housing includes an inside wall formed with a plurality of spaced apart threaded bores and further including:

a mounting board disposed in said interior compartment and formed with a plurality of spaced apart screw bores aligned with the respective said threaded bores;

a plurality of screws received in the respective said screw bores to engage the respective said threaded bores to mount said mounting board to said inside wall; and a plurality of clips on said board for releasably mounting said needle on said board.

26. The vibrating injection device of claim 25 wherein:

said screws are undersized to define respective shanks cooperating with the respective said screw bores to define respective annular spaces therebetween and wherein said device further includes:

a plurality of cushioning bushings received in the respective said annular spaces to cushion movement between said screws and board.

\* \* \* \* \*